(12) United States Patent
Duh et al.

(10) Patent No.: US 8,961,931 B2
(45) Date of Patent: Feb. 24, 2015

(54) 18F-LABELED MONOMERIC GALACTOSE DERIVATIVE USED AS TOMOGRAPHY PROBE

(75) Inventors: Ting-Shien Duh, Taoyuan County (TW); Wuu-Jyh Lin, Taoyuan County (TW); Jenn-Tzong Chen, New Taipei (TW); Li-Yuan Huang, Taoyuan County (TW); Hsin-Ell Wang, Taoyuan County (TW); Chuan-Lin Chen, Taipei (TW); Wen-Yi Chang, Kaohsiung (TW); Hao-Wen Kao, Hsinchu County (TW)

(73) Assignee: Institute of Nuclear Energy Research, Atomic Energy Council, Lungtan, Taoyuan (TW)

( * ) Notice: Subject to any disclaimer, the term of this patent is extended or adjusted under 35 U.S.C. 154(b) by 964 days.

(21) Appl. No.: 13/081,604

(22) Filed: Apr. 7, 2011

(65) Prior Publication Data
US 2012/0259102 A1    Oct. 11, 2012

(51) Int. Cl.
*A61K 51/00*    (2006.01)
*A61M 36/14*    (2006.01)
*C07H 15/18*    (2006.01)

(52) U.S. Cl.
CPC ..................................... *C07H 15/18* (2013.01)
USPC ......................................... 424/1.89; 536/17.9

(58) Field of Classification Search
USPC ........................................................... 424/1.89
See application file for complete search history.

(56) References Cited

PUBLICATIONS

Yang et al. Bioorg. Med. Chem. 17 (2009) 7510-7516.*
Khorev et al. Bioorg. Med. Chem. 16 (2008) 5216-5231.*
Dubber et al. JOC 2000, 65, 5275-5281.*
de Barros et al. Bioorg. Med. Chem. Lett. 20 (2010) 315-317.*
Dimick et al. JACS 1999, 121, 10286-10296.*

* cited by examiner

*Primary Examiner* — Michael G Hartley
*Assistant Examiner* — Sean R Donohue
(74) *Attorney, Agent, or Firm* — Jackson IPG PLLC (57) ABSTRACT

A $^{18}$F-labeled monomeric galactose derivative is provided as a tomography probe. The derivative is a positron emission tomography (PET) probe. The derivative has high affinity and good stability in animal's body. The derivative can be an alternative glucose metabolism imaging agent used in clinic examination and quantification.

3 Claims, 10 Drawing Sheets

| | Normal mice (%ID/organ) | Induced liver fibrosis mice |
|---|---|---|
| Blood | 3.81 ± 0.78 | 6.28 ± 0.97 |
| Heart | 1.64 ± 0.33 | 2.11 ± 0.19 |
| Lung | 1.57 ± 0.44 | 3.19 ± 0.32 |
| Stomach | 1.49 ± 0.25 | 2.03 ± 0.20 |
| Small intestine | 8.29 ± 6.30 | 10.29 ± 1.80 |
| Large intestine | 1.66 ± 0.35 | 1.98 ± 0.42 |
| Spleen | 1.16 ± 0.38 | 1.73 ± 0.19 |
| Pancreas | 1.81 ± 0.49 | 2.88 ± 0.30 |
| Muscle | 1.00 ± 0.24 | 1.20 ± 0.10 |
| Bone | 0.95 ± 0.26 | 1.82 ± 0.16 |
| Kidney | 12.04 ± 3.33 | 25.42 ± 1.92 |
| Bile | 18.41 ± 20.95 | 23.70 ± 14.07 |
| Feces | 1.03 ± 0.53 | 1.02 ± 0.14 |
| Liver | 9.91 ± 0.90 | 9.00 ± 0.72 |
| Liver (%ID/organ) | 11.61 ± 0.76 | 9.37 ± 0.49 |
| Liver-to-blood ratio | 2.67 ± 0.26 | 1.45 ± 0.17 |

FIG. 9

18F-LABELED MONOMERIC GALACTOSE DERIVATIVE USED AS TOMOGRAPHY PROBE

TECHNICAL FIELD OF THE DISCLOSURE

The present disclosure relates to a tomography probe; more particularly, relates to a novel radioactive medicine with its precursor and authentic standard used as a positron emission tomography (PET) probe, where the radioactive medicine has high affinity and has good stability in an animal's body, and where the radioactive medicine can be an alternative glucose metabolism imaging agent used in clinic examination and quantification.

DESCRIPTION OF THE RELATED ARTS

Positron emission tomography (PET) is an important nuclear medicine diagnosis technology. The radioisotope ($^{18}$F) it uses has a relatively long half-live ($t_{1/2}$=110 min) and so has time enough for labeling and diagnosis. Its hydrogen similar property does not involve obvious changes on the space structure and bioactivity of labeled molecular. Hence, $^{18}$F is widely used as a radio imaging agent to label ligand molecular of glucose, amino acid, fatty acid, nucleoside and receptor. PET is used to detect metabolism, protein synthesis and neurotransmitter functional activity and to diagnose tumor, cardiovascular disease, nervous disease and psychosis. Therapy program is further guided and ensured and therapy effect is evaluated. Thus, $^{18}$F is very important to the developments of bio-functional imaging and molecular nuclear medicine.

2-$^{18}$F-Fluoro-2-Deoxy-D-glucose ($^{18}$F-FDG) is the most widely used clinical PET probe. The biological path of its metabolism through glucose is used for diagnosing tumors of brain, heart, etc. and for evaluating therapy effect. However, $^{18}$F-FDG has high absorption ratios in brain, prostate, liver and kidney and thus background is increased, which may make tumor detection difficult and even result in false positive. Besides, $^{18}$F-FDG also has high absorption ratio in inflamed areas, which may result in erroneous diagnosis too. Some tissues of primary liver cancer and clear cell renal cell carcinoma (CCRCC) do not absorb more $^{18}$F-FDG and so false negative may be resulted in. All these limit $^{18}$F-FDG's applications in liver cancer and urinary system tumor. Hence, the prior arts do not fulfill all users' requests on actual use.

SUMMARY OF THE DISCLOSURE

The main purpose of the present disclosure is to provide a novel $^{18}$F-labeled monomeric galactose derivative with its precursor and authentic standard.

The second purpose of the present disclosure is to provide a PET probe with high affinity and good stability in animal's body, where the probe can be an alternative glucose metabolism imaging agent used in clinic examination and quantification.

To achieve the above purposes, the present disclosure is a $^{18}$F-labeled monomeric galactose derivative used as a tomography probe, where $^{18}$F-galactose is provided with its precursor and authentic standard. Accordingly, a novel $^{18}$F-labeled monomeric galactose derivative used as a tomography probe is obtained.

BRIEF DESCRIPTIONS OF THE DRAWINGS

The present disclosure will be better understood from the following detailed description of the preferred embodiment according to the present disclosure, taken in conjunction with the accompanying drawings, in which.

DESCRIPTION OF THE PREFERRED EMBODIMENT

The following description of the preferred embodiment is provided to understand the features and the structures of the present disclosure.

Figure 1:
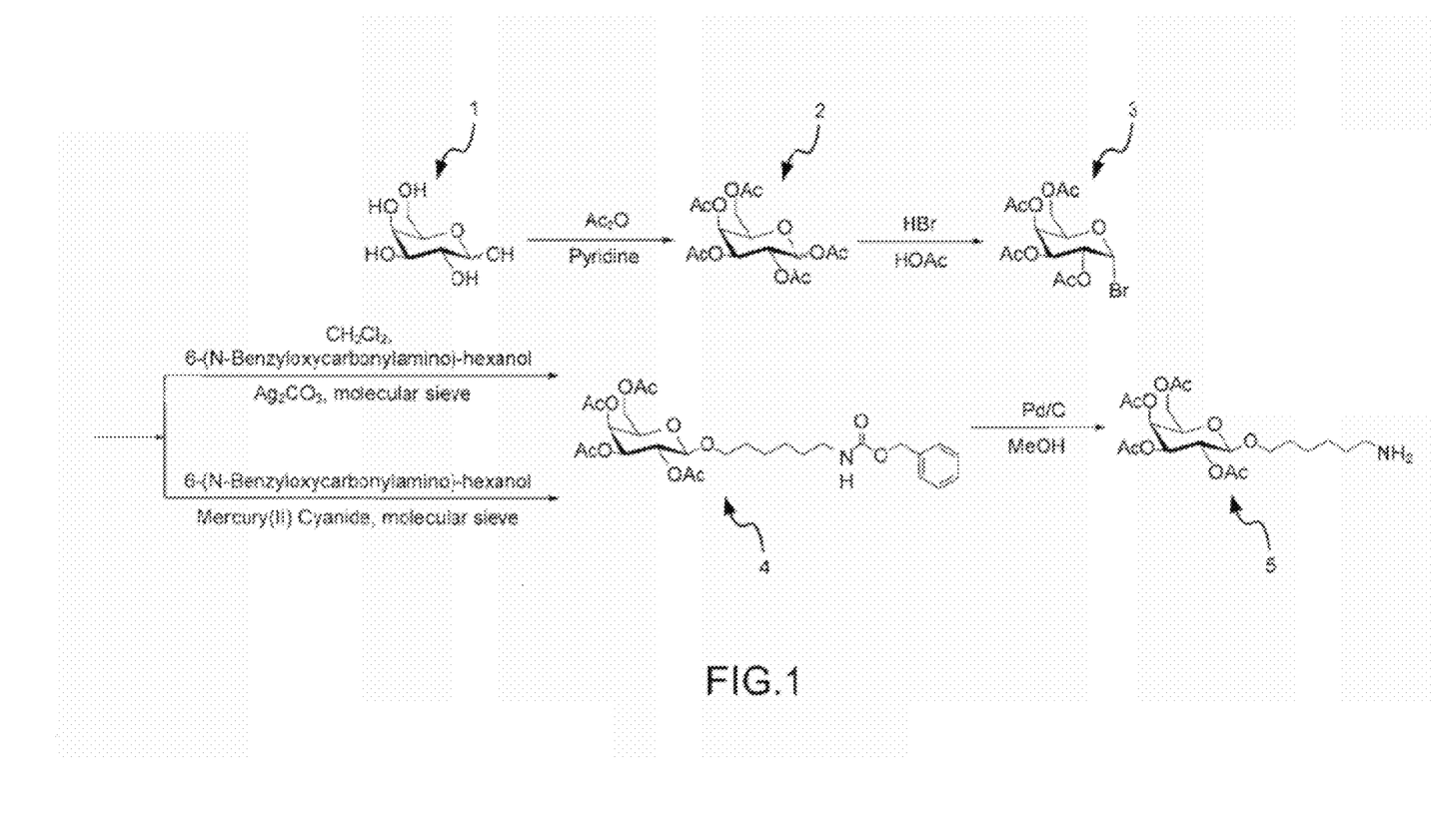
FIG. 1 is the view showing synthesis of the precursor of the preferred embodiment according to the present disclosure.
Figure 2:
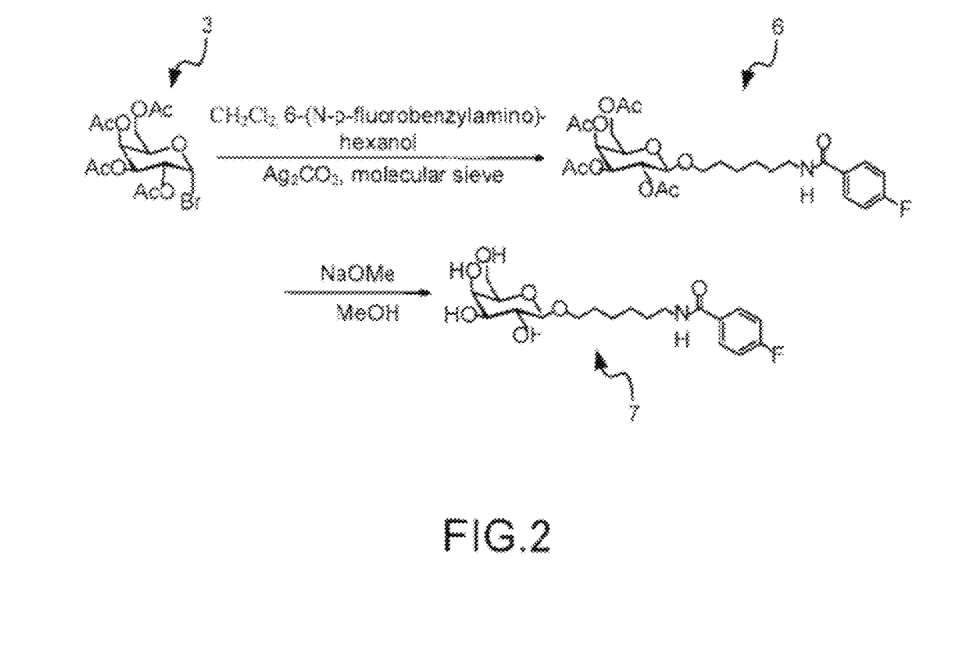
FIG. 2 is the view showing synthesis of the authentic standard.

Please refer to FIG. 1 and FIG. 2, which are views showing syntheses of a precursor and an authentic standard of a preferred embodiment according to the present disclosure. As shown in the figures, the present disclosure is a $^{18}$F-labeled monomeric galactose derivative used as a tomography probe, where the derivative is $^{18}$F-galactose with a precursor (6-amino-1-hexyl-2,3,4,6-tetra-O-acetyl-β-galactopyranoside, shown in FIG. 1) and an authentic standard (6-p-fluorobenzyl-amino-1-hexyl-β-galactopyranoside, shown in FIG. 2) provided.

For synthesizing $^{18}$F-galactose, a precursor and an authentic standard have to be synthesized at first.

In FIG. 1, the precursor is synthesized through the following steps:

(a) Synthesizing β-D-galactosyl pentaacetate 2 g (11.1 mmole) of β-D-galactose 1, 10 mL (106 mmole) of acetic anhydride (AcO$_2$) and 14 ml of anhydrous pyridine are mixed to obtain a solution for reaction by being stirred for 24 hours (hr) at a room temperature. After the reaction, 50 mL of cold water is added to the mixed solution for stopping the reaction by being stirred for 1 hr. Then, the mixed solution is extracted by ethyl acetate (50 mL×3), water (20 mL×3) and brine. After being dried, filtrated, and concentrated by MgSO$_4$, a yellow oil-like product is obtained, which is β-D-galactosyl pentaacetate 2 with a weight of 4.11 g and a yield of 95%. An amount of the reactant is obtained for analysis through thin layer chromatography (TLC) with a stationary phase of Merck silica gel F254 plastic plates and a mobile phase of EA/hexane=3/2, where $R_f$=0.54. The reactant is confirmed through nuclear magnetic resonance (NMR) to be β-D-galactosyl pentaacetate 2 with a result as follows:

$^1$H NMR (CDCl$_3$, 200 MHz): δ 6.34 (s, 1H), 5.69-5.01 (m, 3H), 4.35-3.98 (m, 3H), 2.13, 2.01, 1.99, 1.97, 1.96 (s, 15H, OAc)

(b) Synthesizing 2,3,4,6-tetra-O-acetyl-α-D-galactopyranosyl bromide

In a mixed solution of 3.9 g (10 mmole) of β-D-galactosyl pentaacetate 2 and 100 mL of anhydrous methylene chloride ($CH_2Cl_2$), 4 mL of an acetic acid (HOAc) solution, 4 mL acetic anhydride and 33% liquid HBr are added under 0° C. for reaction for 24 hrs, where temperature for the reaction is raised from 0° C. to a room temperature. After the reaction, cold water is used to stop the reaction and then methylene chloride (50 mL×3) is added. After the solution is dried with $MgSO_4$, filtrated, and concentrated, an organic layer is extracted to obtain a yellow oil-like product, which is 2,3,4, 6-tetra-O-acetyl-α-D-galactopyranosyl bromide 3 with a weight of 4 g and a yield of 98%. An amount of the reactant is obtained for analysis through TLC with a stationary phase of Merck silica gel F254 plastic plates and a mobile phase of EA/hexane=1/2, where $R_f$=0.61. The reactant is confirmed through NMR to be 2,3,4,6-tetra-O-acetyl-α-D-galactopyranosyl bromide 3 with a result as follows:

$^1$H NMR ($CDCl_3$, 200 MHz): δ 6.61 (d, J=4 Hz, 1H), 5.42 (d, J=3 Hz, 1H), 5.33-5.22 (m, 1H), 4.98-4.91 (m, 1H), 4.40 (t, J=6.6 Hz, 1H), 4.08-4.02 (m, 2H), 2.05, 2.01, 1.95, 1.90 (s, 12H, OAc)

(c) Synthesizing 6-(N-Benzyloxycarbonylamino)-hexanol

In a mixed solution of 5 g (42.67 mmol) of 6-aminohexanol, 50 mL of tetrahydrofuran and 15 mL of pure water, 12 mL of 1N sodium hydroxide is used to adjust pH value to 8~9. After the reaction, ether (30 mL×3) is used for extracting an organic layer. The organic layer is dried with $MgSO_4$, filtrated and concentrated to obtain a white crude product. The product is re-crystallized with methylene chloride and n-hexane to obtain a white solid of 6-(N-Benzyloxycarbonylamino)-hexanol with a yield of 90%. An amount of the reactant is obtained for analysis through TLC with a stationary phase of Merck silica gel F254 plastic plates and a mobile phase of ethyl acetate/hexane 1/2, where $R_f$=0.3. The reactant is confirmed through NMR to be 6-(N-Benzyloxycarbonylamino)-hexanol with a result as follows:

$^1$H NMR ($CDCl_3$, 200 MHz): δ 7.32 (brs, 5H, ph-H), 5.06 (s, 2H, ph-$CH_2$), 4.79 (br, NH), 3.549 (t, J=6 Hz, 2H), 3.16 (dd, J=6.4 Hz, J=12.8 Hz, 2H), 1.78-1.33 (m, 8H, $CH_2$)

(d) Synthesizing 6-Cbz-amino-1-hexyl-2,3,4,6-tetra-O-acetyl-β-galactopyranoside

[Method 1]

In 25 mL of a methylene chloride solution having 5 g (12.1 mmole) of 2,3,4,6-tetra-O-acetyl-α-D-galactopyranosyl bromide 3, 4.6 g (13.8 mmole) of 6-(N-Benzyloxycarbonylamino)-hexanol, 3.3 g (12.1 mmole) of $Ag_2CO_3$ and 3.0 g of activated 4 Å molecular sieves are added under 0° C. for reaction for 24 hrs under argon (Ar) gas, where temperature for the reaction is raised from 0° C. to a room temperature. After the reaction, the solution is filtrated with celite and is washed with 15 mL of methylene chloride. An organic layer of the filtered solution is then extracted with 30 mL of saturated sodium bicarbonate ($NaHCO_3$) solution and is dried with $MgSO_4$, filtrated and concentrated to obtain a first crude product. An amount of the reactant is obtained for analysis through TLC with a stationary phase of Merck silica gel F254 plastic plates and a mobile phase of ethyl acetate/hexane=1/2, where $R_f$=0.38. The first crude product is a mixture of α- and β-galactopyranosides. Then, the first crude product is processed through flash chromatography through segregation to obtain a second crude product of β-galactopyranoside, where eluent is ethyl acetate/hexane=1/1. The second crude product is dissolved with 15 mL of methanol (MeOH) and is added with 1 mL of 0.5N sodium methoxide (NaOMe or $NaOCH_3$) in methanol to be processed through deacetylation at a room temperature for 24 hrs. Then, a flash chromatography is processed with an eluent of ethyl acetate/2-propanol=10/1 for obtaining 1.4 g of purified β-galactopyranoside. Then the purified β-galactopyranoside is dissolved in 4 mL of pyridine and is added with 2.86 mL of acetic anhydride for reaction for 24 hrs at a room temperature. After the reaction, 20 mL of cold water is added to stop the reaction to be extracted by ethyl acetate (20 mL×3), 25 mL of water and brine. Then, the reactant is dried with $MgSO_4$, filtrated and concentrated to obtain a yellow oil-like product of 6-Cbz-amino-1-hexyl-2, 3,4,6-tetra-O-acetyl-β-galactopyranoside 4 with a weight of 1.8 g and a yield of 25%.

[Method 2]

4.0 g (20.51 mmol) of 6-(N-Benzyloxycarbonylamino)-hexanol, 2 g of activated 3 Å molecular sieves and 7.77 g of mercury(II) cyanide are dissolved in 30 mL of an acetonitrile solution under Ar gas. After stirring for 15 minutes (min), 12.64 g (30.76 mmol) of 2,3,4,6-tetra-O-acetyl-α-D-galactopyranosyl bromide 3 is added to be dissolved in 20 mL of an acetonitrile solution for reaction for 24 hrs under Ar gas. After the reaction, the solution is filtrated with celite and is concentrated to obtain a third crude product. The third crude product is dissolved in 100 mL of methylene chloride to be extracted with 10% $NaHCO_3$ water solution, 10% potassium iodide (KI) water solution and 10% sodium thiosulfate water solution sequentially for obtaining an organic layer. After drying with $MgSO_4$, filtrating and concentrating, a fourth crude product is obtained to be processed through flash chromatography with an eluent of ethyl acetate/hexane=2/3 for segregation to obtain a yellow oil-like product of 6-Cbz-amino-1-hexyl-2,3,4,6-tetra-O-acetyl-β-galactopyranoside 4 with a weight of 6.78 g and a yield of 63%.

The reactant obtained through either of the above two methods is confirmed through NMR to be 6-Cbz-amino-1-hexyl-2,3,4,6-tetra-O-acetyl-β-galactopyranoside with a result as follows:

$^1$H NMR ($CDCl_3$, 200 MHz): δ 7.31 (s, 5H, ph-H), 5.35 (d, J=3.2 Hz, 1H), 5.21-4.94 (m, 4H), 4.40 (d, J=7.8 Hz, 1H), 4.14-4.06 (m, 2H), 3.88-3.82 (m, 2H), 3.58-3.40 (m, 1H), 3.15-3.09 (m, 2H), 2.14, 2.06, 1.95 (s, 12H, OAc), 1.48-1.22 (m, 8H, $CH_2$)

(e) Synthesizing 6-amino-1-hexyl-2,3,4,6-tetra-O-acetyl-β-galactopyranoside 200 mg (0.343 mmole) of 6-Cbz-amino-1-hexyl-2,3,4,6-tetra-O-acetyl-β-galactopyranoside 4 is dissolved in 1.72 mL of methanol for reaction for 24 hrs with 50 mg of 10% Pd/C catalyst under 1 atm of hydrogen gas. After filtrating with celite, the solution is concentrated to obtain a yellow oil-like product of 6-amino-1-hexyl-2,3,4,6-tetra-O-acetyl-β-galactopyranoside with a weight of 150 mg and a yield of 98%. The reactant is confirmed through NMR to be 6-amino-1-hexyl-2,3,4,6-tetra-O-acetyl-β-galactopyranoside 5 with a result as follows:

$^1$H NMR ($CDCl_3$, 200 MHz): δ 5.32-4.91 (m, 5H), 4.39 (d, J=8 Hz, 1H), 4.11-4.06 (m, 2H), 3.87-3.79 (m, 2H), 3.42-3.38 (m, 1H), 2.77 (br, NH), 2.08, 1.98, 1.91 (s, 12H, OAc), 1.54-1.29 (m, 8H, $CH_2$)

In FIG. 2, an authentic standard of the preferred embodiment, 6-p-fluorobenzyl-amino-1-hexyl-β-galactopyranoside, is synthesized as follows:

(f) Synthesizing 6-amino-1-hexyl-2,3,4,6-tetra-O-acetyl-β-galactopyranoside 1.0 g (8.53 mmole) of 6-aminohexanol is dissolved in a mixed solution of 17 mL of methylene chloride and 3.6 mL (26 mmol) of triethylamine. After 1 mL (8.53 mmol) of p-fluorobenzoyl chloride is slowly added at 0° C., ice-bath is ended to raise temperature to a room temperature for reaction for 12 hrs. After the reaction, cold water is added to stop the reaction and 20 mL of methylene chloride is used to extract an organic layer to be dried with MgSO$_4$, filtrated and concentrated. Then, re-crystallization is processed in a mixed solution of dichloromethane/n-hexane for obtaining a product of 4-fluoro-N-(6-hydroxyhexyl)-benzamide with a weight of 1.83 g and a yield of 90%. The reactant is confirmed through NMR to be 4-fluoro-N-(6-hydroxyhexyl)-benzamide with a result as follows:

$^1$H NMR (CDCl$_3$, 200 MHz): δ 7.78-7.71 (m, 2H, ph-H), 7.12-7.02 (m, 2H, ph-H), 6.23 (br, NH), 3.64-3.58 (m, 2H), 3.46-3.37 (m, 2H), 1.63-1.34 (m, 8H, CH$_2$)

(g) Synthesizing 6-p-fluorobenzyl-amino-1-hexyl-β-galactopyranoside 500 mg (1.21 mmole) of 2,3,4,6-Tetra-O-acetyl-α-D-galacto-pyranosyl bromide 3 is dissolved in 2.5 mL of methylene chloride. After cooling down to 0° C., 438 mg (13.3 mmole) of 4-fluoro-N-(6-hydroxyhexyl)-benzamide, 330 mg (12.1 mmole) of Ag$_2$CO$_3$ and 1 g of activated 4 Å molecular sieves are added for reaction for 24 hrs. After the reaction, the solution is filtrated with celite and washed with 15 mL of methylene chloride. Then, an organic layer is extracted from the solution through 30 mL of saturated NaHCO$_3$ water solution to obtain an intermediate product 6. After being dried with MgSO$_4$, filtrated and concentrated, the intermediate product 6 is dissolved in 1.5 mL of methanol and is added with 0.02 mL of 0.5M NaOMe or NaOCH$_3$ in methanol for reaction for 24 hrs at a room temperature. After the reaction, the solution is filtrated with celite and concentrated to obtain a white solid product of 6-p-fluorobenzyl-amino-1-hexyl-β-galactopyranoside 7 with a weight of 122.4 mg and a yield of 25%. An amount of the product is obtained for analysis through TLC with a stationary phase of Merck silica gel F254 plastic plates and a mobile phase of ethyl acetate/2-propanol=10/2, where R$_f$=0.15. The product is confirmed through NMR to be 6-p-fluorobenzyl-amino-1-hexyl-β-galactopyranoside 7 with a result as follows:

$^1$H NMR (d-MeOH, 200 MHz): δ7.89-7.82 (m, 2H, ph-H), 7.22-7.12 (m, 2H, ph-H), 4.19 (d, J=7 Hz, 1H), 3.95-3.71 (m, 4H), 3.59-3.39 (m, 6H), 1.61-1.41 (m, 8H, CH$_2$)

Figure 3:
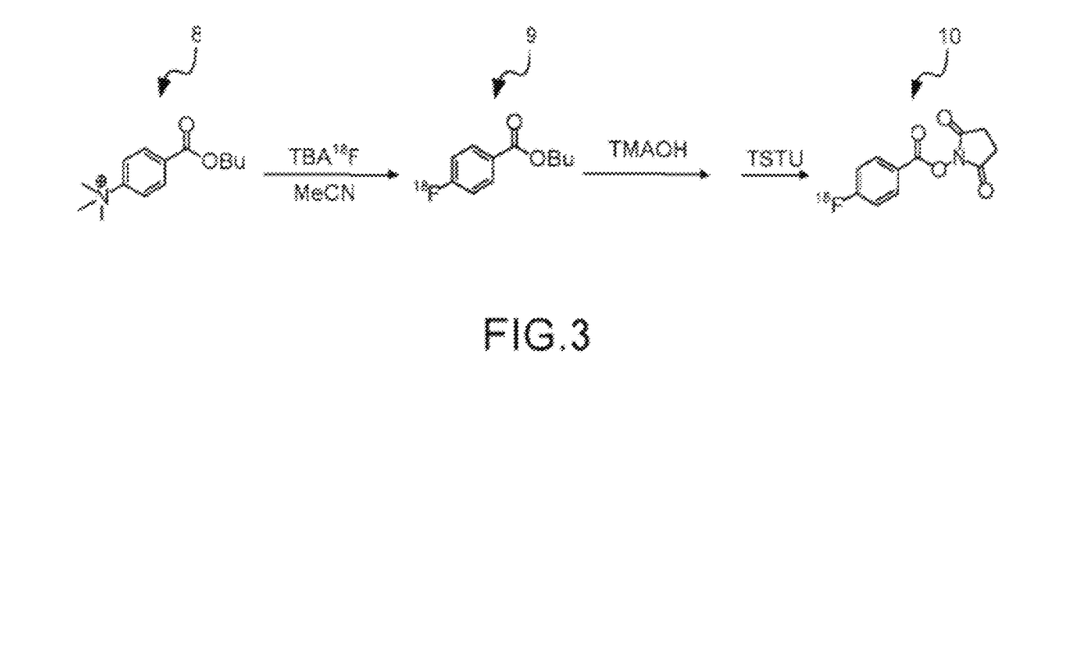
FIG. 3 is the view showing synthesis of the $^{18}$F-SFB.
Figure 4:
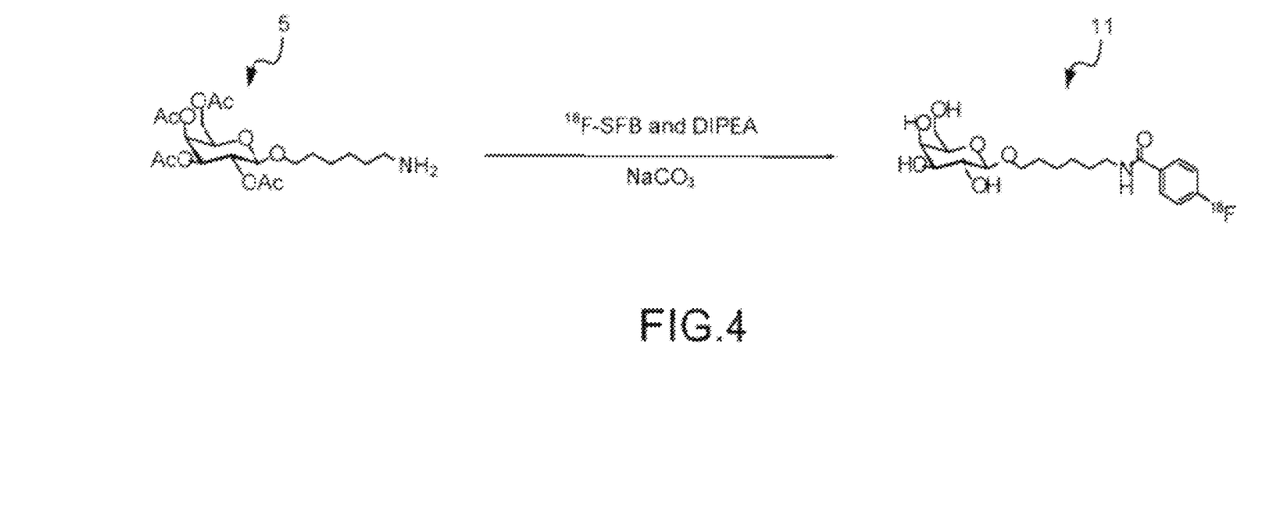
FIG. 4 is the view showing synthesis of the $^{18}$F-labeled monomeric galactose derivative.

Please further refer to FIG. 3 and FIG. 4, which are a view showing syntheses of $^{18}$F-SFB and $^{18}$F-labeled monomeric galactose derivative. As shown in the figures, After obtaining the precursor and the authentic standard of the preferred embodiment, $^{18}$F labeling is processed. At first, $^{18}$F-N-succinimidyl-4-fluorobenzoate ($^{18}$F-SFB) is synthesized through the following steps:

(h) Synthesizing $^{18}$F-SFB

A $^{18}$F-fluoride water solution is passed through a QMA cartridge with 0.8 mL of a bicarbonate solution passed through the QMA cartridge for obtaining a TBA$^{18}$F solution, where the bicarbonate solution has 40 mM tetra-butyl ammonium (TBA). The TBA$^{18}$F solution is put in a sealed V-shaped bottle to be heated under 100° C. Nitrogen gas is flowed in and the bottle is a little vacuumed for fast drying on the liquid surface. 1.8 mL of anhydrous acetonitrile (MeCN) is slowly added into the V-shaped bottle in three different times to be heated under 100° C. with nitrogen gas flowed in at the same time for drying through azeotropy of vapor and acetonitrile. 2 mg of tert-butyl-4-N,N,N-trimethylammoniumbenzoate triflate 8, which is dissolved in 0.8 mL of anhydrous acetonitrile, is added into the V-shaped bottle for reaction for 10 min at 100° C. After the fluorination, a fifth crude product of tert-butyl-$^{18}$F-4-fluorobenzoate 9 is obtained. After temperature of the reaction solution is cooled down to the room temperature, a part of the reactant is taken out to be analyzed through TLC for obtaining a labeling efficiency of $^{18}$F, where a stationary phase of Merck silica gel F254 plastic plates and a mobile phase of ethyl acetate/n-hexane 1/8 are used. 20 μL of 25% methanolic Me4NOH or TMAOH is added into a $^{18}$F-FBA solution for reaction for 10 min under 100° C. After the reaction, the dissolvent is dried at 100° C. and acetonitrile (0.8 mL×2) is added into the reactant for drying through azeotropy of water and acetonitrile. After temperature of the reactant is cooled down to the room temperature, 500 μL of dimethyl sulfoxide with 15 mg of O—(N-succinimidyl)-1,1,3,3-tetramethyluronium tetrafluoroborate (TSTU) dissolved in is added for reaction for 2 min at the room temperature to obtain a crude product of $^{18}$F-SFB. 10 mL of 5% acetic acid is added into the crude product of $^{18}$F-SFB to be passed through a C18 plus cartridge. 10 mL of water is used to elute the C18 plus cartridge at first. The water obtained after the elution is dropped off. Then, 3 mL of acetonitrile is passed through the C18 plus cartridge; thus, a purified $^{18}$F-SFB 10 is obtained. A part of the $^{18}$F-SFB is taken to be analyzed through TLC for obtaining radiochemical purity of the $^{18}$F-SFB, where a stationary phase of Merck silica gel 60 RP-18 F254s plates and a mobile phase of 50% methanol in H$_2$O are used.

In FIG. 4, the $^{18}$F-labeled monomeric galactose derivative is finally synthesized through the following steps:

(i) Synthesizing $^{18}$F-labeled monomeric galactose derivative

The 6-amino-1-hexyl-2,3,4,6-tetra-O-acetyl-β-galactopyranoside 6 is dissolved in 200 μL of acetonitrile to be added with 10 μL of N,N-Diisopropylethylamine (DIPEA) and 18F-SFB 10 for reaction for 30 min under 50° C. After the reaction, 20 μL of 1M NaOMe or NaOCH3 in methanol is added for reaction for 15 min to obtain a $^{18}$F-labelled product 11, which is a $^{18}$F-labeled monomeric galactose derivative: $^{18}$F-galactose. 1N HCl is added to the $^{18}$F-labelled product 11 for neutralization. The $^{18}$F-labelled product 11 is analyzed through high-performance liquid chromatography (HPLC) for obtaining its radiochemical purity by using C18 sieves with a mobile phase of acetonitrile/0.1% acetic acid buffer=1/4 (vol/vol) and a flowing velocity of 0.8 mL/min.

Figure 5A:
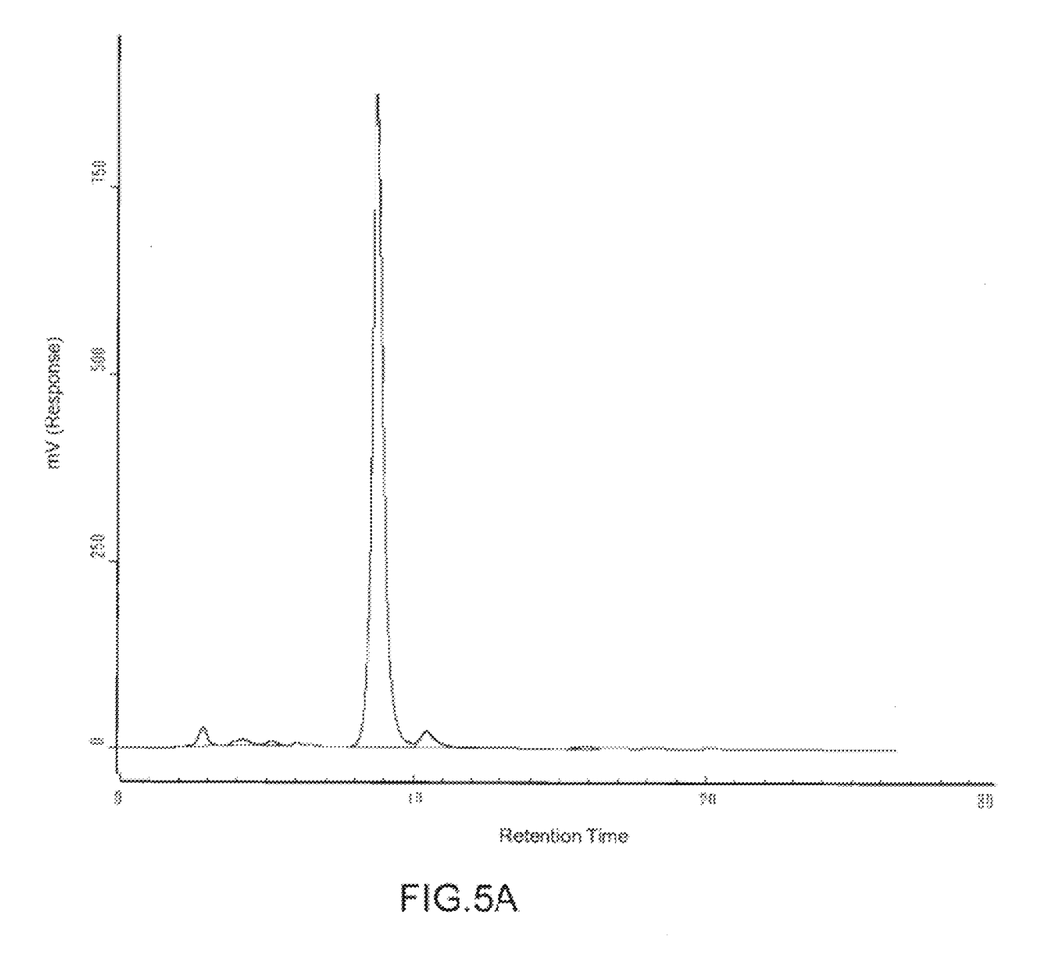
FIG. 5A is the view showing the UV peak of $^{18}$F-galactose.
Figure 5B:
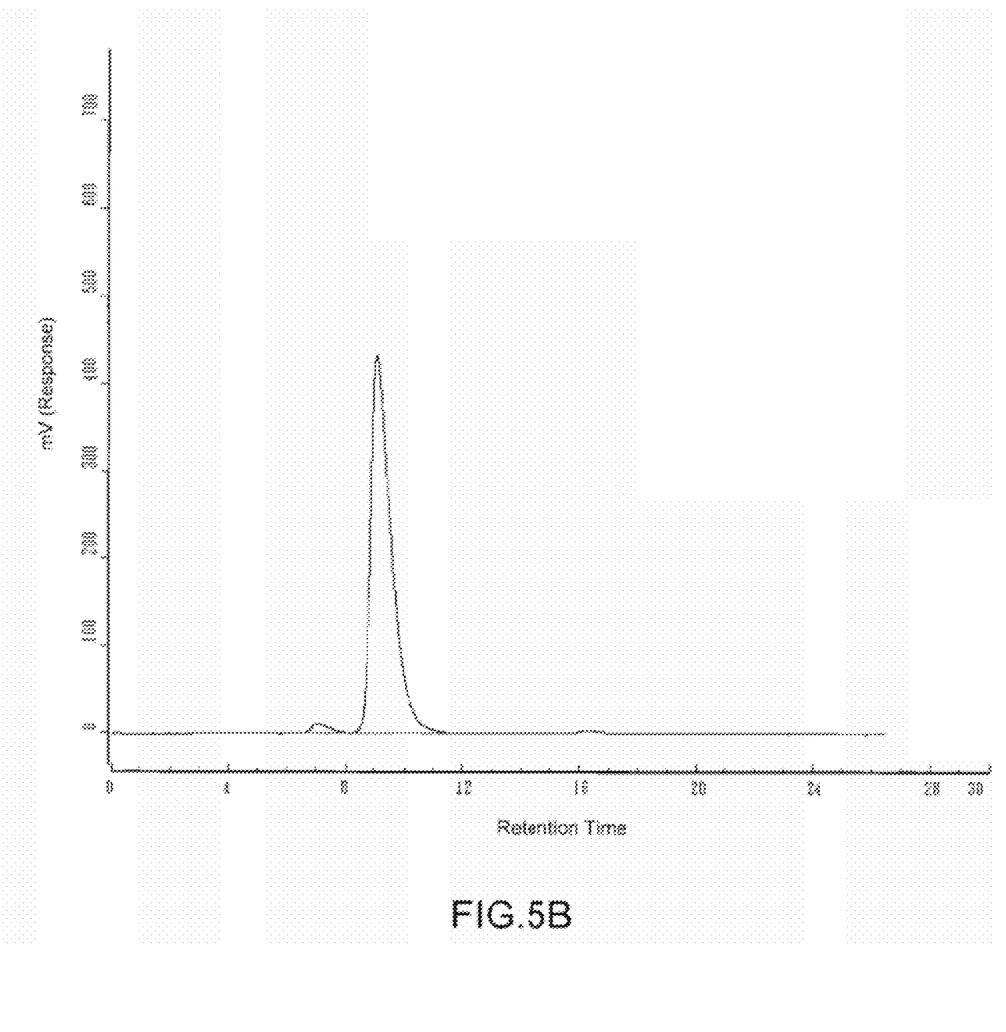
FIG. 5B is the view showing the radio peak of $^{18}$F-galactose.

Please further refer to FIG. 5A and FIG. 5B, which are views showing an UV peak and a radio peak of $^{18}$F-galactose. As shown in the figures, the $^{18}$F-labelled product 11 has a residence time about 9 min and a radiochemical purity greater than 95%. After attenuation calibration, radiochemical yield of the $^{18}$F-labelled product 11 achieves 30~35% and its synthesis time is about 3 hrs.

Figure 6:
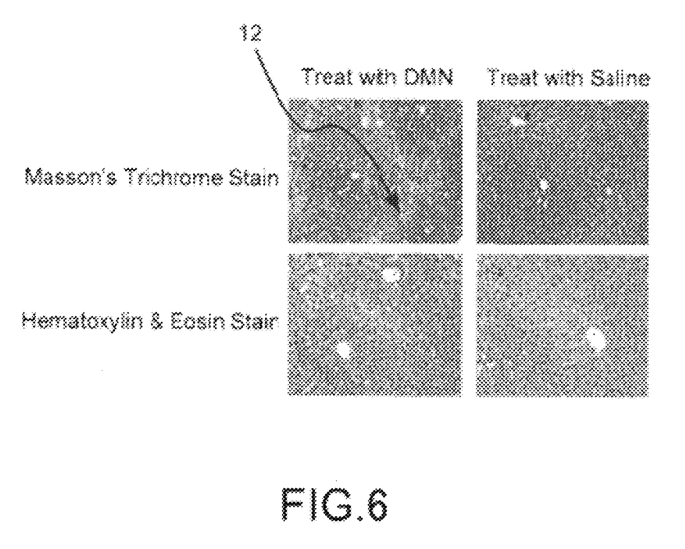
FIG. 6 is the view showing the liver fibrosis of mice dyed through H & E and Masson methods.

Please refer to FIG. 6, which is a view showing liver fibrosis of mice dyed through H & E and Masson methods. As shown in the figures, dimethylnitrosamine (DMN) is used to induce liver fibrosis. 12 mice are randomly divided into two groups each having 6 mice. One is an experimental group and the other is a control group. Mice in the experimental group are injected with 10 mg·kg of DMN for 3 continuous days in a week, and this process lasts for four weeks. Mice in the control group are injected with the same amount of normal saline diluted into a density of 10 mg/ml. During the time for inducing liver fibrosis, all mice are fed with food and water normally. Four days after injecting DMN the final time, dyeing methods of H & E and Masson's are used to examine sliced tissues of mouse bodies for confirming DMN's ability on inducing liver fibrosis of the mice.

For examining the tissues, the mice are sacrificed by blowing high-density $CO_2$ for the mice to breathe in at first. Then, the livers are taken out to sink left lateral lobe in 4% pH 7.4 phosphate-buffered paraformaldehyde. After being paraffin-embedded for 24 hrs, 4 μm of each tissue is taken.

The tissues are examined for their morphological changes through methods of Hematoxylin and Eosin stains and then Masson's trichrome is used to examine statuses of liver fibrosis. In the figure, the mice injected with normal saline show the same statuses as normal mice, where no blue color show in the mice under Masson's method. But, the mice injected with DMN show blue color on fibrosis tissues 12 in the mice; and the average weight of a mouse having fibrosis liver have only 92% weight of a normal mouse.

Figure 7:
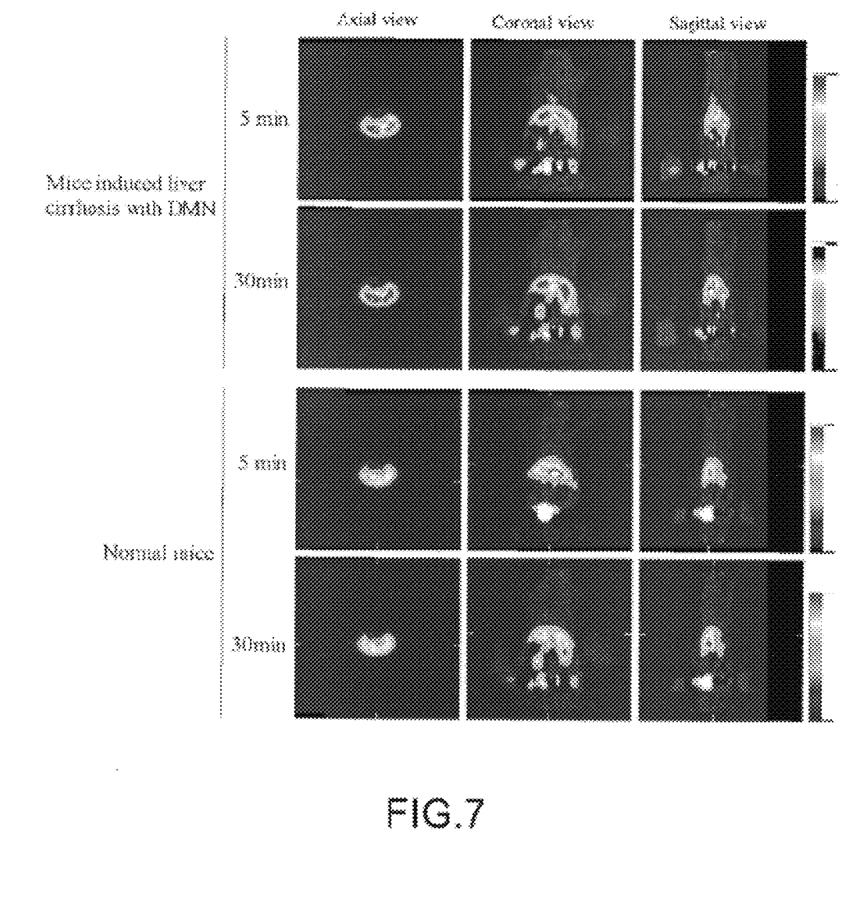
FIG. 7 is the view showing a microPET dynamic image of mice having liver fibrosis.

Please refer to FIG. 7, which is a view showing a microPET dynamic image of mice having fibrous livers. As shown in the figure, a radioactive medicine of 200 μCi of $^{18}$F-galactose is injected into a normal mouse and a mouse having fibrous liver from tail vein at first. After being anaesthetized with isoflurane and injected with the radioactive medicine, a microPET machine (microPET R4 scanner, Concorde Microsystems, Knoxville, Tenn.) is used for dynamic imaging. Through the images obtained after injected with the radioactive medicine for 1 min, 30 min and 1 hr, the ability of $^{18}$F-galactose on being an imaging agent for asialoglycoprotein receptor of a mouse having a fibrous liver is examined.

In the figure, the image taken after being injected for 1 min shows radioactivity mainly on heart and liver, which shows $^{18}$F-galactose is flowed to entire body following blood flow. The image for 30 min shows obvious radioactivity accumulation in liver. The image for 1 hr not only shows radioactivity accumulation in liver but also shows obvious radioactivity accumulation in kidney and bladder, where, after analyzing urine, the radioactivity mainly comes from $^{18}$F-galactose. Hence, it is proved that $^{18}$F-galactose has high stability in animal's body and is mainly excreted by the urinary system.

Figure 8:
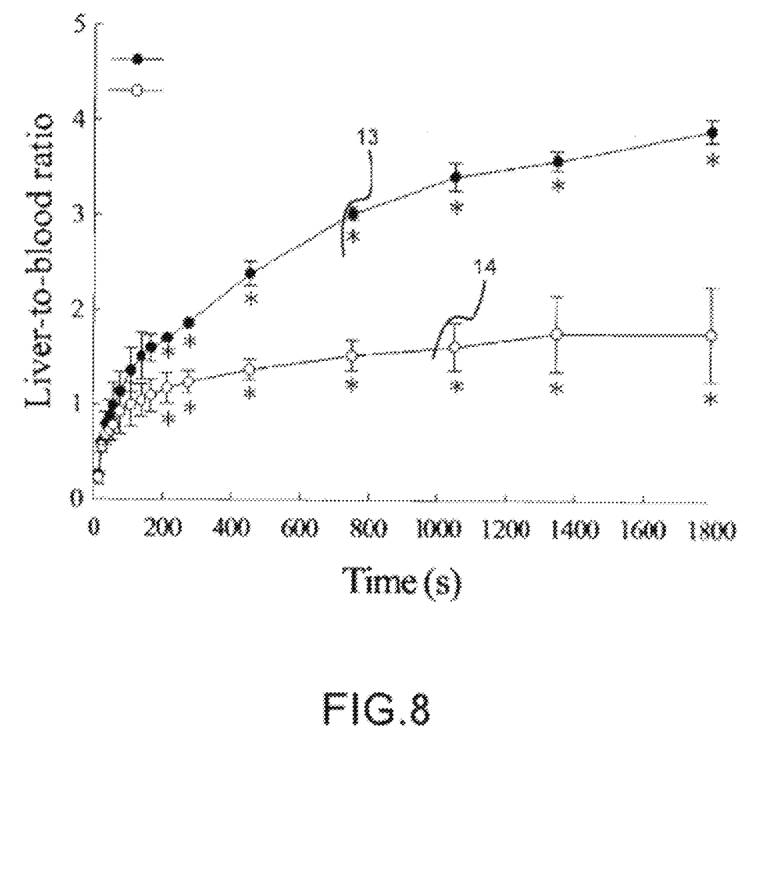
FIG. 8 is the view showing the curve of L/B to time for ROIs of liver and heart.

Please refer to FIG. 8, which is a view showing a curve of L/B to time for ROIs of liver and heart. As shown in the figure, ROIs of liver and heart are obtained to show a curve of liver-to-blood ratio (L/B) to time. A first curve 13 shows L/B for normal mouse and a second curve 14 shows L/B for a mouse having fibrous liver. As a result shows, P=0.042 at 3.5 min after being injected with medicine and P<0.01 thereafter, which means the L/B values for normal mouse and mouse having fibrous liver obviously differs after 3.5 min.

Figure 9:
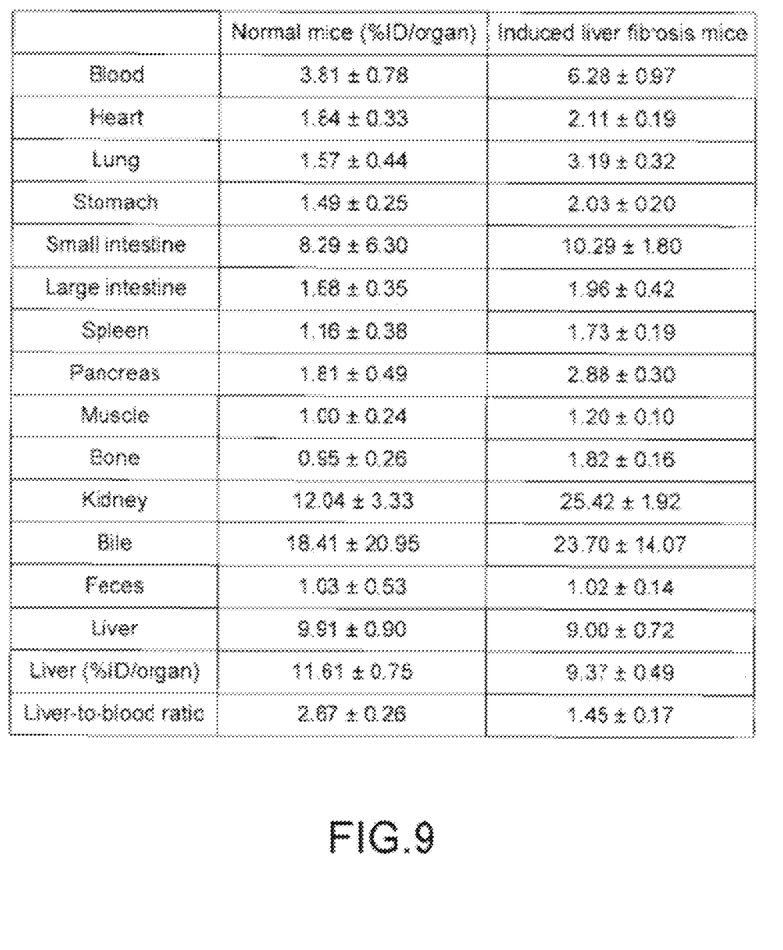
FIG. 9 is the view showing the radioactivities in organs of the mice.

Please refer to FIG. 9, which is a view showing radioactivities in organs of mice. As shown in the figure, a $^{18}$F-labeled monomeric galactose derivative according to the present disclosure is injected into a normal mouse and a mouse having fibrous liver from tail vein. 5 min later, the mice are sacrificed and tissues of organs are obtained to examine their accumulated radioactivities, where results are shown in % ID/organ with n=5. After the injection, radioactivity is found in urine and is accumulated very soon, which shows the $^{18}$F-labeled monomeric galactose derivative is mainly excreted by the urinary system, including kidney and bladder. Besides, in the hepatobiliary system including liver, gallbladder and small intestine, some radioactivity is also found, where the derivative may enter small intestine from gallbladder after being metabolized in liver. Yet, in large intestine and feces, no obvious radioactivity accumulation is found, where time may be too short for the derivative and its metabolized product ($^{18}$F-fluorobenzoic acid, $^{18}$F-FBA) to enter large intestine to be excreted by feces after injection just for 5 min, or both of the derivative and the metabolized product may be water-soluble to be recycled in small intestine and back to the blood system to be excrete from kidney.

By comparing the normal mouse and the mouse having fibrous liver, blood injected with the derivative shows obvious difference after 5 min. It means that, after the derivative enters into the animal's body, absorption is reduced owing to decreasing of asialoglycoprotein receptors in liver and, thus, the derivative is greatly accumulated in circulatory system of the mouse having fibrous liver. The L/B value of the mouse having fibrous liver is lower than that of the normal mouse, which coincides with what shows in microPET image. The other organs of the mouse having fibrous liver also show obvious differences to those of the normal mouse, which may be caused by high accumulation by blood. As is described, the mouse having fibrous liver induced by being injected with DMN has a lower L/B value than the normal mouse and the decreasing of asialoglycoprotein receptors owing to a disease can be detected and quantified by the $^{18}$F-labeled monomeric galactose derivative.

To sum up, the present disclosure is a $^{18}$F-labeled monomeric galactose derivative used as a tomography probe, where a novel radioactive medicine with its precursor and authentic standard is developed as a PET probe; where the radioactive medicine has high affinity and good stability in animal's body, and where the radioactive medicine can be an alternative glucose metabolism imaging agent used in clinic examination and quantification.

The preferred embodiment herein disclosed is not intended to unnecessarily limit the scope of the disclosure. Therefore, simple modifications or variations belonging to the equivalent of the scope of the claims and the instructions disclosed herein for a patent are all within the scope of the present disclosure.

What is claimed is:

1. A $^{18}$F-labeled monomeric galactose derivative used as a tomography probe, which is $^{18}$F-galactose and has a structure of 2. The derivative according to claim 1, wherein said derivative is for use in PET to identify the presence of liver cancer and/or urinary system tumors in a patient.

3. The derivative according to claim 2, wherein the liver cancer is primary liver cancer or clear cell renal cell carcinoma.

* * * * *